(12) United States Patent
Gubelmann et al.

(10) Patent No.: US 6,284,288 B1
(45) Date of Patent: Sep. 4, 2001

(54) USE OF SILICA AS AGENT FOR CONTROLLING THE DEGRADATION OF BICARBONATE, RESULTING MIXTURE AND ITS APPLICATION

(75) Inventors: Michel Gubelmann, Princeton, NJ (US); Michel Seguin, Neuilly-sur-Seine (FR)

(73) Assignee: Novacarb, Paris (FR)

( * ) Notice: Subject to any disclaimer, the term of this patent is extended or adjusted under 35 U.S.C. 154(b) by 0 days.

(21) Appl. No.: 09/214,593

(22) PCT Filed: Jul. 8, 1997

(86) PCT No.: PCT/FR97/01234

§ 371 Date: May 25, 1999

§ 102(e) Date: May 25, 1999

(87) PCT Pub. No.: WO98/01390

PCT Pub. Date: Jan. 15, 1998

(30) Foreign Application Priority Data

Jul. 8, 1996 (FR) .................................................. 96 08458

(51) Int. Cl.[7] ............................ A61K 33/00; A61K 7/00; A61K 7/16

(52) U.S. Cl. ............................ 424/717; 424/401; 424/49; 514/970

(58) Field of Search ...................................... 423/267, 275, 423/420, 422, 430; 106/466, 465, 463; 424/717, 401; 514/970

(56) References Cited

FOREIGN PATENT DOCUMENTS

| 1171752 | * | 6/1964 | (DE) . |
| 15 46 508 | | 12/1966 | (DE) . |
| 1 361 606 | | 10/1964 | (FR) . |

OTHER PUBLICATIONS

Database WPI, Section Ch, Week 9231, Derwent Publications Ltd., London, GB; AN 92–253918 XP002024881 & JP 04 170 315 A, (TOSOH CORP), Jun. 18, 1992.

* cited by examiner

*Primary Examiner*—Shep K. Rose
*Assistant Examiner*—Donna Jagoe
(74) *Attorney, Agent, or Firm*—Burns, Doane, Swecker & Mathis, L.L.P.

(57) ABSTRACT

The use of silica for controlling the thermal degradation of bicarbonate of an alkaline, alkaline-earth metal or bicarbonate of ammonia with an average particle size less than or equal to 100 $\mu$m is disclosed. The resulting bicarbonate and silica mixtures may be used in cosmetics and detergents, and more particularly in formulae for toothpaste.

19 Claims, No Drawings

USE OF SILICA AS AGENT FOR CONTROLLING THE DEGRADATION OF BICARBONATE, RESULTING MIXTURE AND ITS APPLICATION

The subject-matter of the present invention is the use of silica as agent for controlling the thermal degradation of alkali metal, alkaline earth metal or ammonium bicarbonate and the use of the silica/bicarbonate mixtures thus obtained in applications in cosmetics and detergency.

Bicarbonates with a very fine particle size, that is to say less than or equal to 100 μm, are well known constituents of cosmetic and detergent formulations, in particular because of their abrasive and pH-control properties.

However, they exhibit a disadvantage which relates to their thermal degradation temperature. Thermal degradation is understood to mean particularly the temperature at which carbon dioxide is given off. For example, in the preparation of toothpaste formulations, the usual temperature of mixing is of the order of 50° C., in order to avoid any degradation of the bicarbonate which they comprise. Now, it would be advantageous if this temperature could be high, so as to improve the productivity of the process for the formulation of the toothpaste.

In addition, the bicarbonate exhibits another disadvantage related to its very high ability to cake, an ability which becomes increasingly marked as the particle size becomes finer. This in particular presents problems during the use of the said bicarbonate after a more or less lengthy storage. It is therefore necessary to be able to have available a bicarbonate exhibiting a better stability on storage.

These problems and others are solved by the present invention, which therefore consists of the use of silica as a mixture with alkali metal, alkaline earth metal or ammonium bicarbonate with the aim of thermally stabilizing the said bicarbonate, the latter exhibiting a mean particle size of less than or equal to 100 μm.

It has been found, entirely unexpectedly, that bicarbonate with a very fine particle size could be stabilized when it existed as a mixture with silica, not only during storage but also during its use. This is because the bicarbonate thus treated with the additive exhibits an improved flowability with respect to the bicarbonate alone, as well as a decreased ability to cake. In addition, the temperature range in which the bicarbonate degrades, that is to say the temperature range in which departure of carbon dioxide is observed, is shifted towards higher temperatures and their range is broadened.

Finally, the mixture according to the invention exhibits the advantage of being used directly by the user. This is because the composition of the mixture according to the invention is compatible with applications in cosmetics and detergency in particular, such as, for example, the formulation of toothpaste. This allows the applicator to do without an additional stage of metering bicarbonate and silica, while having available a mixture which does not exhibit the disadvantages of the bicarbonate alone.

However, other characteristics and advantages of the present invention will become more clearly apparent on reading the description and examples which will follow.

The first object of the invention is therefore to thermally stabilize the bicarbonate of fine particle size.

The bicarbonate can be an alkali metal, alkaline earth metal or ammonium bicarbonate. More particularly, the stabilized bicarbonate is an alkali metal or alkaline earth metal bicarbonate. The bicarbonate is preferably a sodium bicarbonate.

The mean size of the bicarbonate particles is less than or equal to 100 μm. According to a specific embodiment of the invention, the mean size of the bicarbonate particles is between 10 and 90 μm. More particularly, the mean size of the bicarbonate particles is between 20 and 80 μm and preferably between 20 and 60 μm. The particle size is measured by using an AFNOR sieve or by laser diffraction using a Sympatec particle sizer.

The bicarbonate is generally obtained by employing a process comprising essentially two parts. Thus, in a first stage, alkali metal, alkaline earth metal or ammonium carbonate is prepared, according to the Solvay process for example. In a second part, an aqueous solution is prepared by dissolving the carbonate thus obtained and then carbon dioxide is injected in order to obtain the bicarbonate.

Commercially available bicarbonates are suitable for the present invention. However, the present invention is particularly advantageous in stabilizing bicarbonates with an extra-fine particle size.

The silica will now be described.

According to the present invention, a precipitated silica is more particularly employed.

Precipitated silica is understood to mean here a silica obtained by precipitation from the reaction of an alkaline silicate with an acid, generally an inorganic acid, at an appropriate pH of the precipitation medium. In particular, the pH employed is basic, neutral or only slightly acidic. Any method can be used for the preparation of silica; it can, for example, consist of the addition of acid to a silicate vessel heel or alternatively the complete or partial simultaneous addition of acid or a silicate to a water or silicate solution vessel heel, for example.

Use may be made, in the present invention, of silicas with abrasive or alternatively thickening property. It should be noted that the property of the silica is conventionally dependent on the conditions under which the precipitation is carried out.

According to a preferred embodiment of the invention, the silica employed has an abrasive property.

Silicas which have subsequently been subjected to a calcination stage at high temperature, for example greater than or equal to 450° C., can also be employed.

However, it is preferable to use a silica which has not been subjected to such a treatment.

According to another characteristic of the silica used as stabilizer for the bicarbonate, it exhibits a mean size of the particles of between 8 and 30 μm. More particularly, the mean size of the particles is between 8 and 25 μm and preferably between 10 and 20 μm. The mean size of the particles is generally determined by laser diffraction on a Sympatec particle sizer.

Likewise, the precipitated silica used in the present invention preferably have a BET specific surface of between 140 and 300 $m^2/g$, in particular between 210 and 250 $m^2/g$. The BET specific surface is determined according to the Brunauer-Emmet-Teller method described in "The Journal of the American Chemical Society", vol. 60, page 309, February 1938, which corresponds to ISO Standard 5764/1 (Appendix I).

The silica employed in the present invention preferably exhibits a DOP oil uptake of between 250 and 370 ml/100 g, in particular between 300 and 350 ml/100 g. The DOP oil uptake is determined according to ISO Standard 787/5 by employing dioctyl phthalate.

A silica with a total pore volume of greater than 2.10 $cm^3/g$ is advantageously employed. The total pore volume is generally less than 5 $cm^3/g$. The pore volume can be measured by mercury porosimetry.

The silica employed in the present invention usually exhibits a pH of between 6.8 and 7.5. The pH is measured according to ISO Standard 787/9 (pH of a 5% suspension in water).

Tixosil 43 or Tixosil 103, sold by the company Rhône-Poulenc, is generally used as precipitated silica.

According to another characteristic of the invention, the amount of silica employed is more specifically between 0.1 and 15% by weight with respect to the weight of bicarbonate.

More particularly, the amount of silica varies between 1 and 12% by weight. It is preferably between 2 and 10% by weight and, according to an even more specific embodiment, of between 4 and 10% by weight.

The silica and the bicarbonate can be brought into contact in an entirely advantageous way by simple dry mixing of the two products. Mixers of any type are used, insofar as they make it possible to obtain homogeneous distribution of the silica within the bicarbonate. Use is preferably made of a double-ribbon blender.

Thus, in an entirely advantageous way, it is not necessary to use additional additives, such as binding agents, for example.

It should be noted, in addition, that it would not be departing from the scope of the present invention to mix the two constituents in the presence of an agent which disperses the latter, such as alcohols, for example, and then to dry the mixture under conditions such that the bicarbonate is not decomposed. However, such a contacting operation introduces no specific advantages all requiring the use of equipment and the implementation of additional stages, which further encumbers the process.

It has therefore been found that a simple mechanical mixture of silica and of alkali metal, alkaline earth metal or ammonium bicarbonate exhibited an improved temperature behaviour.

This is because, when the solid mixture according to the invention is subjected to a heat treatment, it is found that the degradation temperature of the bicarbonate, demonstrated by departure of carbon dioxide, is greater than or equal to 95° C. In addition, it is noticed that the temperature range in which the carbon dioxide escapes is broadened, which further supports a thermal stabilization of the said bicarbonate.

The advantage of this is attractive when it is used in formulations in cosmetics and in detergency, such as toothpaste. This is because, in order to avoid the degradation of the bicarbonate, it is common to formulate mixtures comprising suspended bicarbonate at temperatures in the region of 50° C. By employing the mixture according to the invention, it is possible, without risk of releasing carbon dioxide, to prepare such formulations at temperatures which reach 70° C. and more.

Furthermore, it has been noticed that the bicarbonate thus treated with the additive exhibited an improved flowability before and after storage with respect to bicarbonate alone.

This is because the mixture comprising the stabilized bicarbonate according to the invention, more particularly the bicarbonate of extra fine quality, exhibits an instantaneous flowability such that the index i is at least 7 and preferably at least 8.5. Such an index is characteristic of a product which easily flows (i between 4 and 10). It should be noted, for reference, that the same bicarbonate without the additive exhibits an index i of approximately 5.5.

Index i denotes the ratio of the main stress or of the maximum stress which can be achieved during steady flow ($\sigma 1$) to the compressive strength of the product (fc). Furthermore, it should be noted that these flowability measurements are carried out in a shearing cell, such as the Jenike cell.

According to an entirely advantageous alternative form of the present invention, the mixture exhibiting these instantaneous flowability indices comprises a bicarbonate to which has been added 2 to 10% by weight of silica with respect to the weight of bicarbonate and preferably 4 to 10% by weight of silica with respect to the same reference.

Furthermore, the mixture comprising the treated bicarbonate according to the invention, more particularly the bicarbonate of extra fine quality, exhibits a flowability after storage for 7 days of at least 3 and which can even reach 4.5, which classifies the bicarbonate treated with the additive according to the invention among cohesive products, indeed products which readily flow. By way of reference, the same bicarbonate without the additive and after storage for 7 days exhibits an index i in the region of 1, which is characteristic of a cohesive product which does not low.

It has also been found that the sensitivity of the flowability to storage of the mixture was decreased with respect to the same bicarbonate without the additive.

According to an entirely advantageous alternative form of the present invention, the mixture exhibiting these flowability indices after storage comprises bicarbonate to which has been added 2 to 10% by weight of silica with respect to the weight of bicarbonate and preferably 4 to 10% by weight of silica with respect to the same reference.

In addition, as indicated previously, the bicarbonate treated with the additive exhibits a greatly decreased ability to cake with respect to the bicarbonate alone.

The subject-matter of the present invention is likewise a mixture comprising silica and alkali metal, alkaline earth metal or ammonium bicarbonate, this mixture comprising 0.1 to 15% by weight of silica with respect to the weight of bicarbonate and the said bicarbonate exhibiting a mean particle size of less than 100 $\mu$m.

The stabilized bicarbonate according to the invention is more particularly an alkali metal or alkaline earth metal bicarbonate, the first being preferred. The present invention is particularly appropriate for stabilizing sodium bicarbonate.

According to an alternative form of the invention, the mean size of the bicarbonate particles is between 10 and 90 $\mu$m. More particularly, the mean size of the bicarbonate particles is between 20 and 80 $\mu$m and preferably between 20 and 60 $\mu$m.

A particularly appropriate embodiment consists of a mixture comprising bicarbonate of extra fine quality.

Furthermore, according to a more specific embodiment of the invention, the silica content varies between 1 and 12% by weight with respect to the weight of bicarbonate. It is preferably between 2 and 10% by weight and, according to an even more specific embodiment, between 4 and 10% by weight.

The characteristics of this mixture, such as the instantaneous flowability, the flowability after storage for 7 days and the thermal degradation properties of the bicarbonate which it comprises, have been explained above and will not be taken up again in this part.

It is completely surprising that the use of silica in this highly specific range of amount makes it possible to achieve objectives of thermal stabilization, of increase in the flowability and of resistance to caking of a bicarbonate for which the mean size of the particles is very fine, which is a feature which significantly worsens the disadvantages of the bicarbonate.

The alkali metal, alkaline earth metal or ammonium bicarbonate according to the invention can be used in numerous fields.

The mixture is advantageously employed in the preparation of cosmetic and detergent formulations. According to a very particularly appropriate embodiment of the invention, the mixture according to the invention is used in toothpaste formulations.

The amount of mixture according to the invention can be adjusted by a person skilled in the art as a function of the abrasive or buffer compound properties of the bicarbonate present in the said mixture. It can thus vary within wide limits. However, by way of illustration, the content of mixture according to the invention in the formulation is between 10 and 50% by weight of the formulation.

Toothpaste formulations comprise various types of components, such as organic or inorganic thickeners, abrasive compounds, humectants, surfactants, additives such as flavourings, softeners, therapeutic agents, salts, buffer compounds and water.

Mention may be made, as organic thickening agents, of cellulose derivatives, such as carboxymethylcellulose, hydroxyethylcellulose, hydroxypropylcellulose or cellulose ethers, gums, such as, for example, xanthan gum, alginates, carrageenans, or crosslinked polyacrylates, such as Carbopol®.

The content of organic thickening agent is generally between 0.1 and 5% by weight, preferably between 0.4 and 2% by weight, of the formulation.

Mention may be made, as inorganic thickening agents, of thickening silicas, clays or sodium aluminosilicates, for example. It should be noted that, if the stabilized bicarbonate according to the invention is stabilized with thickening silicas, the toothpaste formulation may or may not comprise an additional amount of this type of compound, the adjustment being entirely within the scope of the formulator.

The content of an inorganic thickening agent is between 0 and 12% by weight of the formulation.

Mention may be made, among suitable abrasive compounds, of abrasive silicas, calcium diphosphate dihydrate, calcium carbonate, sodium bicarbonate, calcium bicarbonate, calcium pyrophosphate, alumina, titanium oxide, zinc oxide, tin oxide, talc or kaolin. Here again, if the bicarbonate is stabilized with abrasive silicas, a person skilled in the art can decide whether an additional amount of silica is or is not necessary for the formulation.

The content of an abrasive agent is usually between 10 and 50% by weight of the formulation.

As regards the surfactants, mention may be made, without intending to be restricted, of anionic surfactants, such as, in particular, the sodium, magnesium, ammonium or ethanolamine salts of $C_8$–$C_{18}$ alkyl sulphates, with more particularly sodium lauryl sulphate, $C_8$–$C_{18}$ alkyl sulphosuccinates, such as, for example, dioctyl sodium sulphosuccinate, $C_8$–$C_{18}$ alkyl sulphoacetates, such as sodium lauryl sulphoacetate, $C_8$–$C_{18}$ alkyl sarcosinates, such as sodium lauryl sarcosinate, $C_8$–$C_{18}$ alkyl phosphates which can optionally comprise up to 10 ethylene oxide and/or propylene oxide units, or sulphated monoglycerides, alone or as mixtures.

Mention may be made, as non-ionic surfactants, by way of example, of optionally polyethoxylated fatty acids of sorbitan, ethoxylated fatty acids, or esters of polyethylene glycol, alone or as mixtures.

Mention may be made, as suitable amphoteric surfactants, of betaines or sulphobetaines, alone or as mixtures.

The toothpaste formulations generally comprise an amount of surfactants of between 0.1 and 10%, preferably between 1 and 5%, by weight of the formulation.

The formulation can additionally comprise one or more humectants, such as glycerol, sorbitol, polyethylene glycols, lactilol or xylitol, in particular.

The content of humectant is generally between 10 and 70% by weight of the formulation.

The formulation can also comprise bactericidal, antimicrobial or anti-plaque therapeutic agents, such as, for example, zinc citrate, polyphosphates or guanidines.

Flavouring agents, such as essence of aniseed, of mint, of Chinese anise, of juniper or of cinnamon, inter alia, as well as sweeteners, colorants (chlorophyll), preservatives, and the like, are likewise generally used in toothpaste formulations.

Finally, the formulations comprise water in the proportion of 5 to 50% by weight of the formulation, preferably of 10 to 40% by weight of the formulation.

These formulations are prepared conventionally by mixing each of the constituents of the formulation, the advantage being to employ the stabilized bicarbonate according to the present invention.

Concrete but non-limiting examples of the invention will now be presented.

EXAMPLE 1

Preparation of the Silica-Sodium Bicarbonate Mixture.

A mixture is prepared comprising 7% by weight of Tixosil 103 silica (Rhône-Poulenc), with respect to the weight of sodium bicarbonate of extra fine quality (Rhône-Poulenc).

The operation is carried out in a double-ribbon blender comprising an outer ribbon against the wall and an inner ribbon with an opposite pitch.

The rotational speed of the two ribbons is 31 revolutions/minute.

The duration of the mixing is 30 minutes.

EXAMPLE 2

Instantaneous Flowability Measurements.

The instantaneous flowability was evaluated, using a Jenike shearing cell, for the mixture according to Example 1, after its preparation, and a control sample, decaked bicarbonate of extra fine quality.

The index i, corresponding to the ratio of the main stress or of the maximum stress which can be achieved during steady flow ($\sigma 1$) to the compressive strength of the product (fc), was determined for each of the samples, according to the invention and control.

The results are collated below:
Control: 5.6
Mixture according to the invention: 8.8

A sharp improvement in the flowability index of the mixture according to the invention is observed.

EXAMPLE 3

Thermogravimetric Measures.

The thermal degradation characteristics (departure of $CO_2$) of the mixture of Example 1 and of the control sample were measured in a thermobalance by total decomposition under argon.

The temperature range is between 0 and 500° C. with a temperature gradient of +5° C./min.

The device is coupled to a mass spectrometer, in order to record the temperature range for release of carbon dioxide.

The temperature ranges in which carbon dioxide is released are as follows:
Control: 90–200° C.
Mixture according to the invention: 100–210° C.

A significant shift in the temperature range in which the bicarbonate is decomposed is observed, showing that the mixture according to the invention is stabilized with respect to the control sample.

What is claimed is:

1. A method for controlling the thermal degradation of alkali metal bicarbonate, alkaline earth metal bicarbonate or ammonium bicarbonate, wherein the mean size of bicarbonate particles is in the range of 20–100 μm, said method comprising mixing an effective amount of silica having a mean particle size in the range of 8–30 μm with said bicarbonate to control the thermal degradation of said bicarbonate.

2. The method according to claim 1, wherein the mean size of the bicarbonate is between 20 and 80 μm.

3. The method according to claim 1, wherein the mixture exhibits an instantaneous flowability such that the index i is at least 7.

4. The method according to claim 3, wherein the index i is at least 8.5.

5. The method according to claim 1, wherein the mixture exhibits a flowability after storage for 7 days of at least 3.

6. The method according to claim 1, wherein the amount of silica is between 0.1 and 15% by weight with respect to the weight of bicarbonate.

7. The method according to claim 6, wherein silica is between 1 and 12% by weight.

8. The method according to claim 7, wherein the silica is between 1 and 10% by weight.

9. The method according to claim 1, wherein the silica is between 2 and 10% by weight.

10. The method according to claim 1, wherein the BET specific surface of the silica is between 140 and 300 $m^2/g$.

11. The method according to claim 1, wherein the silica and the bicarbonate are dry mixed.

12. A mixture of silica and alkali metal bicarbonate, alkaline earth metal bicarbonate or ammonium bicarbonate, comprising 0.1 to 15% by weight, with respect to the weight of the bicarbonate, of silica having a mean particle size in the range of 8–30 μm and said bicarbonate exhibits a mean particle size in the range of 20–100 μm.

13. The mixture according to claim 12, wherein the thermal degradation temperature of the bicarbonate is greater than 95° C.

14. The mixture according to claim 12, which exhibits an instantaneous flowability such that the index i is at least 7.

15. The mixture according to claim 14, wherein the index i is at least 8.5.

16. The mixture according to claim 12, which exhibits a flowability after storage for 7 days of at least 3.

17. A cosmetic formulation comprising an effective amount of the mixture according to claim 12 and a cosmetically acceptable carrier.

18. A detergent formulation comprising an amount of the mixture according to claim 12 and a carrier.

19. A toothpaste formulation comprising an effective amount of the mixture according to claim 12 and an acceptable carrier.

* * * * *